United States Patent [19]  [11]  4,149,080
Schittenhelm  [45]  Apr. 10, 1979

[54] TOMOGRAPHIC APPARATUS FOR THE PRODUCTION OF TRANSVERSE TOMOGRAPHIC IMAGES

[75] Inventor: Rudolf Schittenhelm, Erlangen, Fed. Rep. of Germany

[73] Assignee: Siemens Aktiengesellschaft, Munich & Berlin, Fed. Rep. of Germany

[21] Appl. No.: 814,556

[22] Filed: Jul. 11, 1977

[30] Foreign Application Priority Data

Sep. 23, 1976 [DE] Fed. Rep. of Germany ....... 2642846

[51] Int. Cl.² ............................................... A61B 6/02
[52] U.S. Cl. .................................. 250/445 T; 250/369
[58] Field of Search ..................................... 250/445 T

[56] References Cited
U.S. PATENT DOCUMENTS 3,937,965  2/1976  Vasseur ........................... 250/445 T Primary Examiner—Alfred E. Smith
Assistant Examiner—T. N. Grigsby
Attorney, Agent, or Firm—Hill, Gross, Simpson, Van Santen, Steadman, Chiara & Simpson

[57] ABSTRACT

In one illustrated embodiment two detector arrays are arranged in parallel and only one detector array is impinged upon by the primary radiation beam, the second detector array detecting only the scatter radiation due to the primary beam. Preferably, the second detector array is arranged so as to receive substantially a maximum intensity essentially equal to the scatter radiation impinging on the first detector array. In one example, the output of the second detector array may be simply subtracted from the output of the first detector array so as to obtain an accurate measure of the transmitted primary radiation. In an alternative embodiment, a single detector array is shifted to a second position for detecting only scatter radiation substantially corresponding to the scatter radiation mixed with the transmitted primary radiation.

1 Claim, 4 Drawing Figures

TOMOGRAPHIC APPARATUS FOR THE PRODUCTION OF TRANSVERSE TOMOGRAPHIC IMAGES

BACKGROUND OF THE INVENTION

The invention relates to a tomographic apparatus for the production of transverse tomographic images of a radiographic subject, comprising a radiation measuring arrangement including a radiation source which produces a fan-shaped beam of rays penetrating the exposure subject, and whose cross-sectional extent, perpendicular to the layer plane, is equal to the layer thickness, and which is of such a magnitude in the layer plane that the entire exposure subject is permeated, as well as including a radiation receiver which determines the radiation intensity behind the subject, as well as comprising a drive mechanism for the measuring arrangement for producing rotational movements, and comprising a measured value converter for the transformation of the signals supplied by the radiation receiver into a tomographic image, wherein the radiation receiver consists of a number of individual detectors.

A tomographic apparatus of this type is e.g. described in the U.S. Pat. No. 3,778,614. In this tomographic apparatus, a rotation of the measuring arrangement through an angle of approximately 360 degrees is prudent for the purpose of producing the input signals of the measured valve converter. What is disadvantageous in the case of the known tomographic apparatus is that not only the primary radiation issuing directly from the radiation source, but also scatter radiation emitted from the exposure subject acts upon the radiation receiver. This stray radiation also produces output signals from the radiation receiver, so that the output signal of a detector of the radiation receiver is made up of a component originating from the primary radiation and representing the attenuation of the radiation through the exposure subject, and a component originating from the stray radiation which is undesired because it invalidates the tomographic image constructed by the measured value converter.

SUMMARY OF THE INVENTION

A principal object of the invention consists in constructing a tomographic apparatus of the type initially cited such that the scatter radiation can be taken into account during the course of image construction.

In one embodiment of the invention, this object is achieved by virtue of the fact that the radiation receiver consists of two detector arrays arranged adjacently and parallel to one another, and that said radiation receiver is arranged such that only one detector array is impinged upon by the primary radiation beam, whereas the second detector array detects (or picks up) only the stray radiation, and that there is provided in the measured value converter a circuit arrangement for correcting the output signals of the detector array impinged upon by the primary radiation beam, this correction being effected by the output signals of the second detector array. This embodiment of the invention, wherein the signals used by the measured value converter for the image construction are to a great extend free of components originating from stray radiation, requires the same scan time as a tomographic apparatus without the inventive second detector array for correcting the output signals of the detector array impinged upon by the primary x-radiation.

The object underlying the invention can, however, also be achieved in that there are provided means for moving the radiation receiver forming a detector array into a second position in which it lies directly next to the radiation beam, and detects only the stray radiation, and that there is provided in the measured value converter a circuit arrangement for correcting the output signals of the radiation receiver with are delivered when the radiation receiver lies in the radiation beam, said correction being effected by the output signals of the radiation receiver supplied in the second position. In the case of this embodiment, a single detector array suffices which is displaced by mechanical means.

Other objects, features and advantages of the invention will be apparent from the following detailed description taken in connection with the accompanying sheets of drawings.

DETAILED DESCRIPTION

Figure 1:
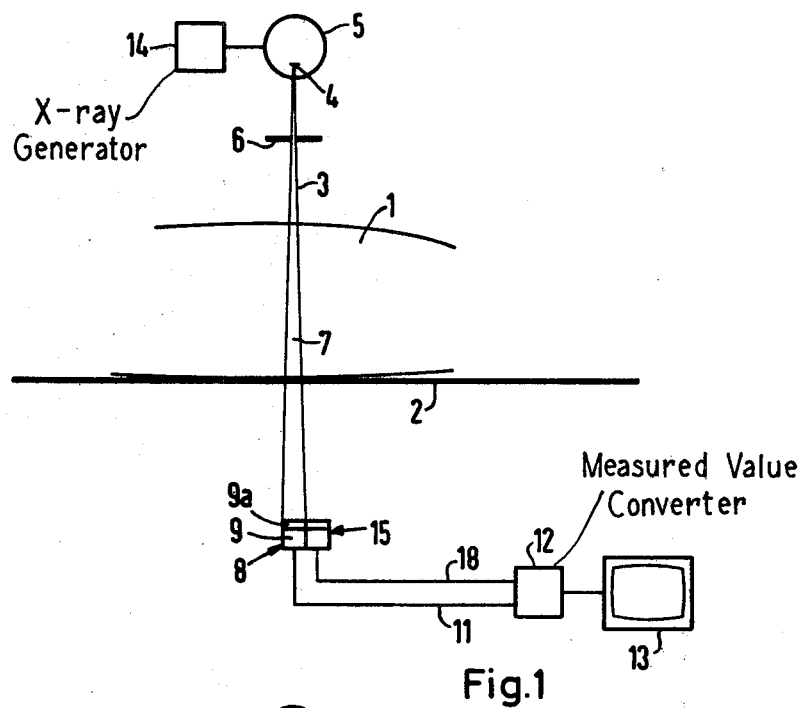
FIGS. 1 and 2 illustrate two different views of a tomographic apparatus in accordance with the invention, the parts which are especially significant in terms of the invention being shown by means of a diagrammatic longitudinal sectional view in FIG. 1, and by means of a transverse sectional view in FIG. 2.
Figure 2:
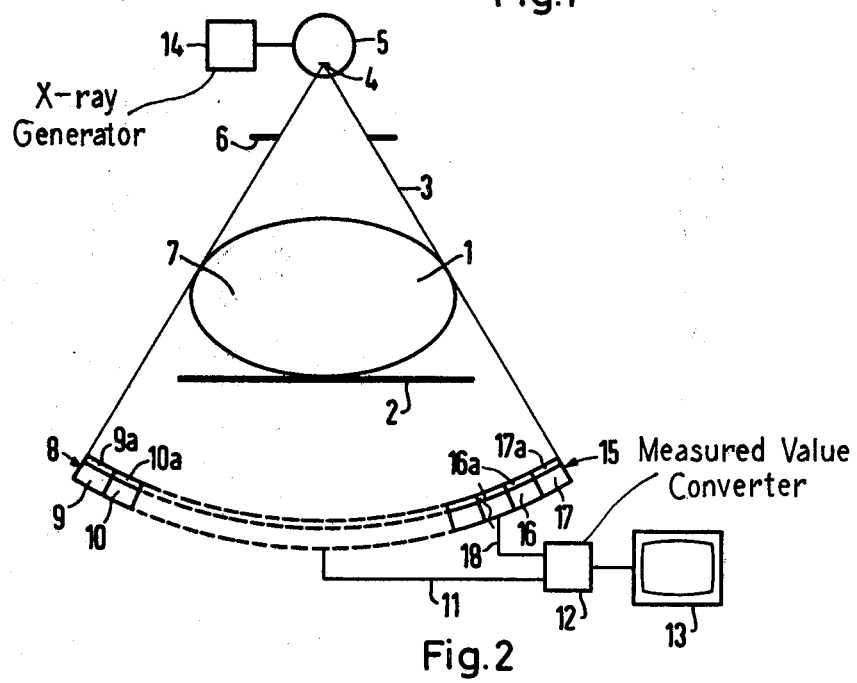

In the sample embodiment, the radiation penetrating the patient is x-radiation. FIGS. 1 and 2 illustrate tomographic apparatus in association with a patient 1, shown in longitudinal outline in FIG. 1 and in cross-sectional outline in FIG. 2, the patient 1 being supported on a couch 2 that is permeable to an x-ray beam 3. The x-ray beam 3 originates from focus 4 of an x-ray tube 5 and is delineated by a primary radiation diaphragm 6 such that its cross-sectional dimension, perpendicular to the examined body layer 7, is equal to the layer thickness and such that a body layer corresponding to the entire patient cross section may be subject to measurement. Viewed in the direction of radiation, there is arranged behind the patient a radiation receiver 8 which consists of a number of detectors 9, 10 etc., arranged in a row (or array). A collimator 9a, 10a, etc. is arranged in front of each of the detectors 9, 10, etc. The number of detectors 9, 10, etc., is selected in compliance with the desired image resolution and may amount to e.g. 256. Radiation receiver 8 is rigidly connected with the x-ray tube 5, and, in order to scan the patient 1; namely, layer 7, measuring arrangement 5, 8, is rotated through 360 degrees about patient 1. The output signals delivered under these conditions be detectors 9, 10,, etc., are supplied by way of a line 11 to a measured value converter 12 which contains a computer which computes an image of the irradiated body layer. In order to reproduce this image, measured value converter 12 is connected to a visual display unit 13. X-ray tube 5 is connected to an x-ray generator 14 which supplies the necessary high voltage.

Figure 3:
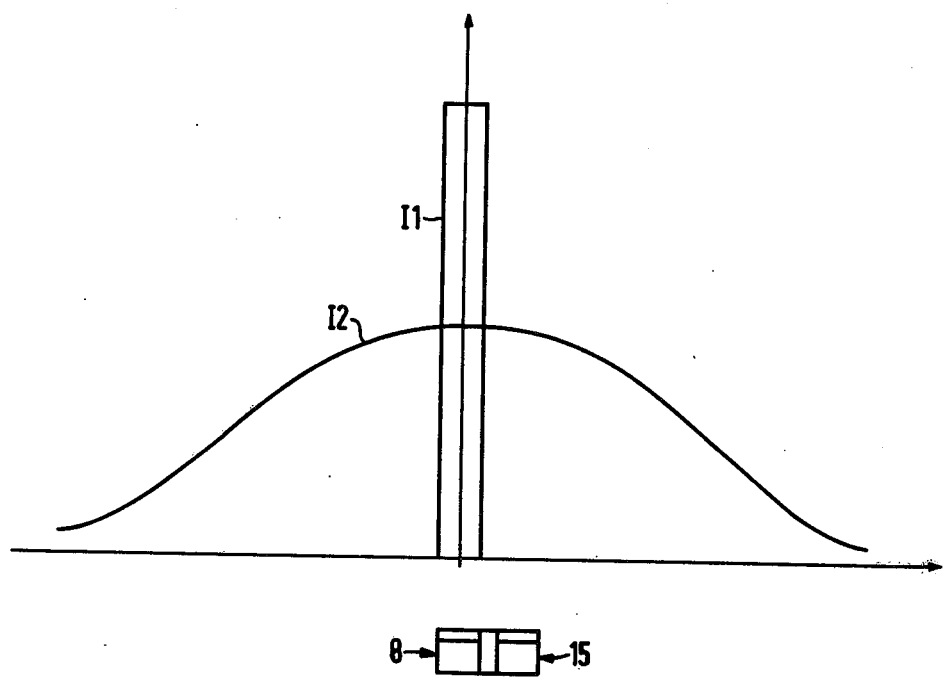
FIG. 3 is an illustration for the purpose of elucidating the apparatus according to FIGS. 1 and 2.

FIG. 3 illustrates the curve of the intensity of the x-radiation at the radiation receiver 8 in the longitudinal direction of couch 2 and in a specific position of measuring arrangement 5, 8.

The radiation intensity is made up of an intensity component I1 and an intensity component I2. Intensity I1 is the intensity of the primary radiation, intensity I2 being the intensity of the secondary radiation emanating from the patient 1. It is clearly apparent that the stray radiation intensity I2 reaches a maximum at points in alignment with the radiation receiver 8 and that there is a drop-off at both sides of the radiation receiver 8 which is initially relatively gradual and then becomes more pronounced.

In order to take into account the stray radiation intensity I2, there is arranged parallel to the radiation receiver 8 and along side the latter a radiation receiver 15 which also consists of an array of detectors, of which detectors 16 and 17 are visible in FIG. 2. A collimator 16a, 17a, etc., is again arranged in front of each of the detectors 16, 17, etc. The radiation receiver 15 does not detect the primary radiation beam 3, but only the secondary radiation which is virtually equal to the secondary radiation which acts upon (or influences) the radiation receiver 8 used for the actual measurement. Dimensions, position, and the total number of the detectors in radiation receiver 15 may differ as compared with detector 8. The output signals of the radiation receiver 15 are supplied via a line 18 to the measured value converter 12. The measured value converter 12 contains a circuit arrangement for correcting the output signals of radiation receiver 8 by means of the output signals of radiation receiver 15 such that the fraction of the output signals of radiation receiver 8 originating from the stray radiation is eliminated. For the simultaneous scanning of several layers, several radiation receivers of the type 8 may be arranged in succession, there being inserted after every two receivers, respectively, one receiver of the type 15 which permits the stray radiation correction of the adjacent receivers 8.

If it is possible to make allowance for a lengthening of the scan time and an increase in the dose on patient 1 in the instance wherein only radiation receiver 8 is present, it is possible to do without the additional radiation receiver 15 if there are means provided for moving radiation receiver 8 into a second position in which it lies directly alongside x-ray beam 3; i.e., occupying the position of radiation receiver 15. In this case, there then takes place in measured value converter 12 a correction of the output signals of radiation receiver 8 which are delivered when radiation receiver 8 is impinged upon by x-ray beam 3, said correction being effected by the output signals delivered when the radiation receiver 8 lies alongside the x-ray beam 3 and is impinged upon only by scatter radiation. The measuring operation may then proceed such that, in predetermined angular positions, e.g. with each angular degree, a measurement first proceeds in the one position of radiation receiver 8 and is then followed by a measurement in the second position of radiation receiver 8. However, it is also conceivable to scan the patient twice through an angle of 360 degrees; namely, first in the one and then in the other position of radiation receiver 8.

In the example, according to FIGS. 1 and 2, radiation receiver 15 does not need to manifest the same number of detectors as radiation receiver 8. In order to effect a correction of the output signals of radiation receiver 8, it is sufficient if the number of detectors or radiation receiver 15 is substantially smaller than the number of detectors of radiation receiver 8.

The scatter radiation signals are deducted from the measuring signals in measured value converter 12.

Figure 4:
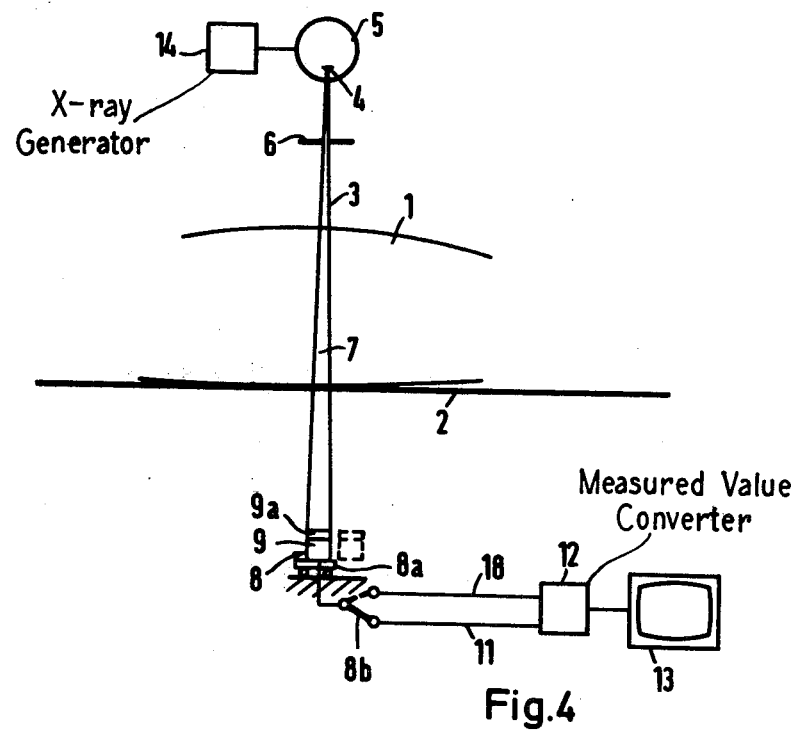
FIG. 4 is a variant of the tomographic apparatus according to FIGS. 1 and 2, the significant parts being shown by means of a diagrammatic longitudinal sectional view.

A sample embodiment wherein a single radiation receiver is present which is alternately moveable (or displaceable) into a position in which it detects the direct x-ray beam 3 or in which it detects the scatter radiation is illustrated in FIG. 4. In FIG. 4, components which are equivalent to components of the sample embodiment according to FIGS. 1 and 2, are designated with the same reference characters. Only one single radiation receiver is provided which is capable of displacement on a carriage 8a perpendicular to the irradiated body layer of patient 1; i.e. in the longitudinal direction of couch 2, from the fully illustrated position into the position illustrated by broken lines. In the fully illustrated position, it detects the direct x-ray beam 3, and in the position illustrated in broken lines, it detects only the scatter radiation. Accordingly, radiation receiver 8, in the fully illustrated position, is connected via a switch 8b with line 11, and in the position illustrated by broken lines, with line 18. In this example, the measured value converter 12 contains a memory which first stores the output signals of radiation receiver 8 in its fully illustrated position, and then subtracts from these output signals the output signals delivered in the position illustrated by broken lines.

It will be apparent that many modifications and variations may be effected without departing from the scope of the novel concepts and teachings of the present invention.

I claim as my invention:

1. Tomographic X-ray apparatus for the production of transverse tomographic images of an exposure subject, comprising a radiation measuring arrangement including a radiation source which produces a fan-shaped primary radiation beam penetrating the exposure subject, the cross-sectional extent of this radiation beam, perpendicular to the layer plane, being equal to the layer thickness, and a radiation receiver which determines the radiation intensity behind the subject, and a measured value converter for transforming the signals delivered by the radiation receiver into a tomographic image, the radiation receiver comprising a number of individual detectors, characterized in that there are provided means for moving the radiation receiver forming one detector array into a second position in which it lies directly alongside the radiation beam and detects only the scatter radiation, and the measured value converter being operable for correcting the output signals of the radiation receiver which are formed when the radiation receiver lies in the radiation beam, said correction of these output signals being effected by the output signals formed in the second position.

* * * * *